United States Patent
Dabir et al.

(10) Patent No.: US 8,292,920 B2
(45) Date of Patent: Oct. 23, 2012

(54) SICKLE NEEDLE AND METHOD

(75) Inventors: Reza Dabir, Grosse Pointe Farms, MI (US); Michael Primavera, Milford, CT (US); Gregg Krehel, Newtown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1730 days.

(21) Appl. No.: 11/272,555

(22) Filed: Nov. 10, 2005

(65) Prior Publication Data

US 2007/0106329 A1     May 10, 2007

(51) Int. Cl.
    *A61B 17/06*     (2006.01)

(52) U.S. Cl. .................................... 606/222; 606/148

(58) Field of Classification Search .................. 606/104, 606/144, 148, 147, 142, 222, 139, 223, 213, 606/145, 157, 149, 232, 205, 153, 155; 604/174, 604/175; 600/201, 205
See application file for complete search history.

(56) References Cited

U.S. PATENT DOCUMENTS

| | | | |
|---|---|---|---|
| 1,377,359 A | 5/1921 | Littlejohn | |
| 1,592,897 A | 7/1926 | Morton | |
| 2,092,292 A | 9/1937 | Stitt | |
| 2,336,689 A | 12/1943 | Karle | |
| 2,811,157 A * | 10/1957 | Kurtz et. al. | 606/223 |
| 2,841,150 A | 7/1958 | Riall | |
| 2,865,375 A | 12/1958 | Banks et al. | |
| 2,865,376 A | 12/1958 | Pellier et al. | |
| 3,038,475 A | 6/1962 | Orcutt | |
| 3,197,997 A | 8/1965 | Kurtz | |
| 3,265,070 A | 8/1966 | Kurtz | |
| 3,592,196 A | 7/1971 | Daikhovsky | |
| 3,636,956 A | 1/1972 | Schneider | |
| 3,799,169 A | 3/1974 | Beroff et al. | |
| 3,840,015 A | 10/1974 | Gain | |
| 3,875,946 A | 4/1975 | Duncan | |
| 3,890,975 A | 6/1975 | McGregor | |
| 3,949,756 A | 4/1976 | Ace | |
| 3,963,031 A | 6/1976 | Hunter | |
| 3,980,177 A | 9/1976 | McGregor | |

(Continued)

FOREIGN PATENT DOCUMENTS

EP     0 494 644 A2     7/1992

(Continued)

OTHER PUBLICATIONS

European Search Report for EP 06023334.3 date of completion is Mar. 19, 2007 (11 pgs).

*Primary Examiner* — S. Thomas Hughes
*Assistant Examiner* — Julie A Szpira

(57) ABSTRACT

A surgical needle which is particularly suited for use in limited space applications and a method for its use are disclosed. The surgical needle generally includes an arcuate portion having a first end and a second end. A pointed tip is disposed near the first end. There is a relatively short, straight shank near the second end of the arcuate portion which extends from the arcuate portion at a predetermined angle. The predetermined angle is defined by the intersection of the arcuate portion and the shank. This predetermined angle is within a range of about 23° to about 29°. In a particularly useful embodiment, the predetermined angle is approximately 26°. Further, an extrapolation of a longitudinal axis of the shank intersects the arcuate portion of the surgical needle.

15 Claims, 5 Drawing Sheets

U.S. PATENT DOCUMENTS

| | | | |
|---|---|---|---|
| 4,010,756 A | | 3/1977 | DuMont et al. |
| 4,034,763 A | | 7/1977 | Frazier |
| 4,054,144 A | | 10/1977 | Hoffman et al. |
| 4,072,041 A | | 2/1978 | Hoffman et al. |
| 4,127,133 A | | 11/1978 | Martinez |
| 4,128,351 A | | 12/1978 | Kurtz et al. |
| 4,204,542 A | | 5/1980 | Bokros et al. |
| 4,237,892 A | | 12/1980 | Ritter et al. |
| 4,345,601 A | | 8/1982 | Fukuda |
| 4,359,053 A | | 11/1982 | Benjamin |
| 4,524,771 A | * | 6/1985 | McGregor et al. ............ 606/223 |
| 4,527,564 A | | 7/1985 | Eguchi et al. |
| 4,587,202 A | | 5/1986 | Borysko |
| 4,660,559 A | | 4/1987 | McGregor et al. |
| 4,672,734 A | | 6/1987 | Kawada et al. |
| 4,777,096 A | | 10/1988 | Borysko |
| 4,799,483 A | | 1/1989 | Kraff |
| 4,799,484 A | | 1/1989 | Smith et al. |
| 4,805,292 A | | 2/1989 | Noguchi |
| 4,880,002 A | | 11/1989 | MacGregor |
| 4,890,614 A | | 1/1990 | Kawada et al. |
| 4,901,721 A | | 2/1990 | Hakki |
| 4,901,722 A | | 2/1990 | Noguchi |
| 4,922,904 A | | 5/1990 | Uetake et al. |
| 4,932,961 A | | 6/1990 | Wong et al. |
| 4,932,962 A | | 6/1990 | Yoon et al. |
| 4,932,963 A | | 6/1990 | Ritter et al. |
| 4,935,029 A | | 6/1990 | Matsutani et al. |
| 4,959,068 A | | 9/1990 | Bendel et al. |
| 4,968,362 A | | 11/1990 | Prasad |
| 4,976,727 A | | 12/1990 | Matsutani et al. |
| 4,981,149 A | | 1/1991 | Yoon et al. |
| 5,001,323 A | | 3/1991 | Matsutani et al. |
| 5,030,228 A | | 7/1991 | Wong et al. |
| 5,041,127 A | | 8/1991 | Troutman |
| 5,059,207 A | | 10/1991 | Shah |
| 5,070,874 A | | 12/1991 | Yoon |
| 5,080,667 A | | 1/1992 | Chen et al. |
| 5,089,011 A | | 2/1992 | Korthoff |
| 5,089,012 A | | 2/1992 | Prou |
| 5,100,431 A | | 3/1992 | Buster et al. |
| 5,100,432 A | | 3/1992 | Matsutani |
| 5,102,418 A | | 4/1992 | Granger et al. |
| 5,123,910 A | | 6/1992 | McIntosh |
| 5,178,628 A | | 1/1993 | Otsuka et al. |
| 5,180,385 A | | 1/1993 | Sontag |
| 5,201,701 A | | 4/1993 | Roettger et al. |
| 5,201,760 A | | 4/1993 | West |
| 5,224,955 A | | 7/1993 | West |
| 5,230,352 A | | 7/1993 | Putnam et al. |
| 5,235,443 A | | 8/1993 | Sontag |
| 5,269,808 A | | 12/1993 | Proto et al. |
| 5,330,441 A | | 7/1994 | Prasad et al. |
| 5,333,625 A | | 8/1994 | Klein |
| 5,336,239 A | | 8/1994 | Gimpelson |
| 5,342,397 A | | 8/1994 | Guido |
| 5,358,498 A | | 10/1994 | Shave |
| 5,364,407 A | | 11/1994 | Poll |
| 5,382,257 A | | 1/1995 | Lewis et al. |
| 5,403,345 A | | 4/1995 | Spingler |
| 5,411,613 A | | 5/1995 | Rizk et al. |
| 5,425,746 A | | 6/1995 | Proto et al. |
| 5,433,728 A | * | 7/1995 | Kim, II ........................ 606/223 |
| 5,437,680 A | | 8/1995 | Yoon |
| 5,450,860 A | | 9/1995 | O'Connor |
| 5,463,292 A | | 10/1995 | Wada |
| 5,468,251 A | | 11/1995 | Buelna |
| 5,477,604 A | | 12/1995 | Smith et al. |
| 5,478,327 A | | 12/1995 | McGregor et al. |
| 5,533,982 A | | 7/1996 | Rizk et al. |
| 5,549,629 A | | 8/1996 | Thomas et al. |
| 5,601,475 A | | 2/1997 | Stametz et al. |
| 5,630,268 A | | 5/1997 | Smith et al. |
| 5,649,961 A | | 7/1997 | McGregor et al. |
| 5,661,893 A | | 9/1997 | Smith et al. |
| 5,667,528 A | | 9/1997 | Colligan |
| 5,683,415 A | | 11/1997 | Brunken |
| 5,683,416 A | | 11/1997 | McGregor et al. |
| 5,693,072 A | | 12/1997 | McIntosh |
| 5,716,392 A | | 2/1998 | Bourgeois et al. |
| 5,725,555 A | * | 3/1998 | Moll ............................ 606/223 |
| 5,741,279 A | | 4/1998 | Gordon et al. |
| 5,741,299 A | | 4/1998 | Rudt |
| 5,776,268 A | | 7/1998 | McJames et al. |
| 5,782,864 A | | 7/1998 | Lizardi |
| 5,797,961 A | | 8/1998 | Smith et al. |
| 5,830,234 A | | 11/1998 | Wojciechowicz et al. |
| 5,853,423 A | | 12/1998 | McGregor et al. |
| 5,879,371 A | | 3/1999 | Gardiner et al. |
| 5,891,164 A | * | 4/1999 | Dabir et al. ................... 606/222 |
| 5,893,592 A | | 4/1999 | Schulze et al. |
| 5,897,572 A | * | 4/1999 | Schulsinger et al. ......... 606/224 |
| 5,913,875 A | | 6/1999 | Smith et al. |
| 5,928,268 A | | 7/1999 | Butwell et al. |
| 5,935,138 A | | 8/1999 | McJames, II et al. |
| 5,937,504 A | | 8/1999 | Esteves et al. |
| 5,984,933 A | | 11/1999 | Yoon |
| 6,018,860 A | | 2/2000 | Smith et al. |
| 6,019,781 A | | 2/2000 | Worland |
| 6,159,233 A | | 12/2000 | Matsuzawa |
| 6,264,675 B1 | | 7/2001 | Brotz |
| 6,322,581 B1 | | 11/2001 | Fukuda et al. |
| 6,514,030 B1 | | 2/2003 | Young et al. |
| 6,588,409 B2 | | 7/2003 | Maloney et al. |
| 6,641,593 B1 | | 11/2003 | Schaller et al. |
| 6,723,107 B1 | | 4/2004 | Skiba et al. |
| 6,749,616 B1 | | 6/2004 | Nath |
| 6,855,159 B1 | | 2/2005 | Tanner et al. |
| 6,877,352 B1 | | 4/2005 | Schlereth |
| 7,118,583 B2 | * | 10/2006 | O'Quinn et al. .............. 606/139 |
| 2002/0193809 A1 | | 12/2002 | Meade et al. |
| 2003/0074022 A1 | | 4/2003 | Roby |
| 2003/0083695 A1 | | 5/2003 | Morris et al. |
| 2003/0093118 A1 | | 5/2003 | Ho et al. |
| 2003/0114883 A1 | | 6/2003 | Roby et al. |
| 2003/0120308 A1 | | 6/2003 | Loubens et al. |
| 2003/0171777 A1 | | 9/2003 | Roby et al. |
| 2004/0059379 A1 | | 3/2004 | Cunningham |
| 2004/0068292 A1 | | 4/2004 | Koscki |
| 2004/0106949 A1 | | 6/2004 | Cohn et al. |
| 2004/0116962 A1 | | 6/2004 | Batke et al. |
| 2004/0116963 A1 | | 6/2004 | Lattouf |
| 2004/0122472 A1 | | 6/2004 | Collier et al. |
| 2004/0127941 A1 | * | 7/2004 | Cunningham et al. ........ 606/223 |
| 2004/0176802 A1 | | 9/2004 | Skiba et al. |
| 2004/0199185 A1 | | 10/2004 | Davignon |
| 2005/0070959 A1 | | 3/2005 | Cichocki, Jr. |

FOREIGN PATENT DOCUMENTS

| | | | |
|---|---|---|---|
| EP | | 494644 A2 * | 7/1992 |
| EP | | 0 852 930 A2 | 7/1998 |

* cited by examiner

SICKLE NEEDLE AND METHOD

BACKGROUND

1. Field of the Invention

The present disclosure relates generally to surgical needles and, more particularly, to a surgical needle and method particularly suited for use in limited space applications, such as cardiovascular, vascular and microvascular surgery.

2. Background of the Art

Various shapes and styles of surgical needles have been developed for use with specific suturing procedures. The needle configurations may vary according to the type of tissue to be sutured and the manner of manipulating the needle during suturing. For example, one such needle used for suturing deep fascia tissue is disclosed in U.S. Pat. No. 5,433,728 to Kim. The needles in accordance with the '728 patent have an arcuate body with a pointed tip. The body forms an arc of approximately 180° to 230° and is joined to a relatively straight shank by a gently curving arcuate neck.

Another specific needle configuration is disclosed in European Patent Application No. 0494644 A2. The needles disclosed in this application are for use in abdominal surgery. One embodiment includes a straight section which bends downwardly at approximately 22° and then curves upwardly with a radius of $5/12^{ths}$ of the overall length of the needle.

A further type of surgical needle configuration, referred to as a "sickle needle," is disclosed in U.S. Pat. No. 5,891,164. The surgical needle disclosed in the '164 patent includes an arcuate portion and a shank portion connected thereto. There is an abrupt angle between these two portions and the angle is between 30° and 70°. This type of needle may be used when a surgeon has limited space in which to work, such as cardiovascular, vascular and microvascular surgery.

In performing cardiovascular, vascular and microvascular surgery, it is often necessary to join two hollow organ or vascular tissue sections together. This is most often accomplished by suturing opposing edges of the vascular tissue sections together. Rather than using a sickle needle, surgeons may use a needle having a substantially constant radius to suture such edges together. Most often the arc of the needle has a pointed tip at one end and a tail portion at an opposite end which is drilled to retain an end of a length of suture material therein.

In order to suture two opposing vascular tissue sections together with prior art surgical needles of the type described above with reference to U.S. Pat. No. 5,433,728 and European Patent Application No. 0494644 A2, the suturing needle is typically held near its tail portion by a needle holder and rotated about the center of its radius through the tissue sections to be joined. For example, in order to suture two vascular tissue sections together, the two vascular tissue sections are approximated and the surgical needle having a length of suture attached thereto is rotated to cause the pointed tip to pierce through an outer wall of a first vascular tissue section and into its lumen. The needle is then further rotated to move the pointed tip of the needle through a lumen of the second vascular tissue section and out through an outer wall of the second vascular tissue section. Once the pointed tip has penetrated through the wall of the second vascular tissue section, the pointed tip is grasped with a needle holder and the tail portion is released.

In order to draw the length of suture through the two vascular tissue sections and remove the needle from the vascular tissue sections, it is necessary to continue to rotate the surgical needle further in approximately a half-circle drawing the suture material through the tissue sections. Since during the entire surgical procedure the needle must be rotated through approximately a complete circle, an operating space having a height more than half of the radius of the needle must be available adjacent the accessed vascular tissue sections.

When a surgeon is performing cardiovascular, vascular and microvascular surgical procedures, a very limited amount of space adjacent the accessed tissue sections is available for manipulation of the surgical needle. There exists a need for a cardiovascular, vascular and microvascular surgical suturing needle configured to be manipulated within a limited space.

SUMMARY

The present disclosure is directed to a surgical needle that is particularly suited for use in limited space applications and a method for its use. The surgical needle generally includes an arcuate portion having a first end and a second end. A pointed tip is disposed near the first end. There is a relatively short, straight shank near a second end of the arcuate portion. The shank extends from the arcuate portion at a predetermined angle. The predetermined angle is defined by the intersection (i.e., juncture) of a tangent of the arcuate portion and the shank.

This predetermined angle is within a range of about 23° to about 29°. In a particularly useful embodiment, the predetermined angle is approximately 26°. As discussed below, reducing the predetermined angle allows the intersection and shank to more easily pass through the tissue, thereby minimizing any potential trauma to such tissue. Furthermore, reducing its predetermined angle results in an extrapolation of a longitudinal axis of the shank to intersect the arcuate portion of the surgical needle. In a particularly useful embodiment, the distance from the extrapolation of the longitudinal axis of the shank to the pointed tip is about 0.100 inches.

The arcuate portion has a constant or variable radius of curvature from the juncture with the shank toward the pointed tip. In the embodiment where the radius of curvature is constant, it may be in the range of about 85° to about 110°. In a particularly useful embodiment, the radius of curvature is about 100°. In the embodiment where the radius of curvature is variable, it may increase from below 100° at the second end of the arcuate portion to above 100° at the first end of the arcuate portion. It may be particularly useful for the radius of curvature to increase from about 85° at the second end of the arcuate portion to about 150° at the first end of the arcuate portion.

The arcuate portion of surgical needle may have a cross-section that is generally circular. The arcuate portion may also be dimensioned such that opposing sides of the cross-section are substantially flat. It is also envisioned that only a portion of arcuate portion has such a cross-section. It is also envisioned that only one side of the cross-section of the arcuate section is substantially flat. Other cross-sectional configurations are also applicable and are contemplated by this disclosure.

The shank may have a substantially circular cross-section and may have a countersunk bore disposed therein for suture attachment. A suture may be attached to the bore using any number of various known techniques, such as, for example, crimping, medical grade adhesives, etc. The length of the shank may be in the range of about 0.078 to about 0.108 inches.

A method of using the surgical needle is also disclosed. The method includes initially grasping the shank of the surgical needle with a needle holder. The pointed tip of the surgical needle is then forced against the wall of a first tissue section and driven into the lumen. The surgical needle is then manipulated to advance the pointed tip and arcuate portion through the first lumen into a second lumen of the second vascular tissue section. The pointed tip is manipulated to penetrate the wall of the second vascular tissue section and to protrude from an outer wall thereof. The pointed tip of the surgical needle is grasped with a needle holder and the shank is released. The surgical needle is then pulled substantially parallel to an outer surface of the second vascular tissue section to thereby draw the surgical needle through the entrance hole and out the exit hole to form a stitch. It is envisioned that a plurality of stitches are made directly after the first stitch. Such a method may only require a portion of the arcuate portion to be pulled from the second lumen before the pointed tip is inserted again.

BRIEF DESCRIPTION OF THE DRAWINGS

Embodiments of the present disclosure are described hereinbelow with reference to the drawings wherein.

DETAILED DESCRIPTION

Figure 1:
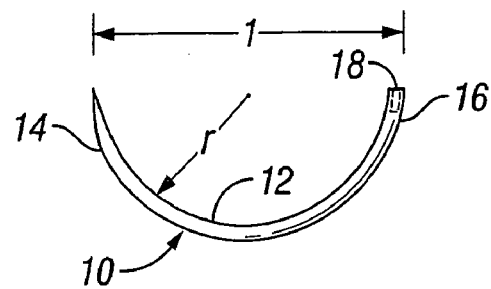
FIG. 1 is a front view of a prior art surgical needle.

FIGS. 1-6, designated "Prior Art," illustrate a surgical suturing needle of the prior art. Referring initially to FIG. 1, there is shown a prior art surgical suturing needle 10 of the type typically used in cardiovascular, vascular and microvascular surgery. Needle 10 generally includes an arcuate body 12 typically having a constant radius of curvature "r." A pointed tip 14 is formed on one end of arcuate body 12 and a tail portion 16 is formed on an opposite end of arcuate body 12. Tail portion 16 includes a suture bore 18 for receipt of an end of a length of suture material therein. When used in cardiovascular, vascular and microvascular applications, needle 10 most preferably has an overall length "l" of about 0.328 to about 0.338 inches and a radius "r" on the order of about 0.1 to about 2.0 inches. While surgical needle 10 is illustrated as forming half a circle with constant radius, prior art surgical needles are also available in styles forming greater or less than half of a circular arc, for example, three eights of a circular arc.

Referring now to FIGS. 2-6, a brief description of the method of suturing an opposed pair of vascular tissue sections utilizing the prior art surgical needle 10 will now be described. As noted hereinabove, suturing with surgical needle 10 typically requires that surgical needle 10 be rotated almost completely about its center of radius, thus necessitating a significant amount of operating space adjacent the vascular tissue sections to be sutured.

Figure 2:
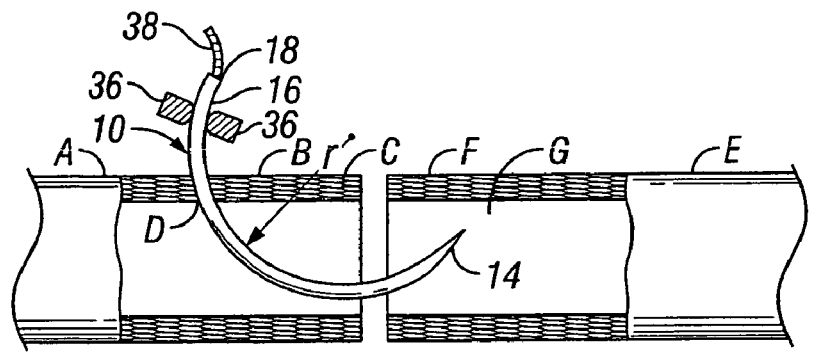
FIGS. 2-6 illustrate the prior art surgical needle of FIG. 1 in various stages of being drawn through tissue.

Referring to FIG. 2, to suture two vascular tissue sections A and E together, a distal end of first vascular tissue section A having a wall B defining a lumen C therein is approximated adjacent a distal end of a second vascular tissue section E having a wall F and defining a lumen G therein. Tail portion 16 of surgical needle 10 is grasped with a needle holder 36 to manipulate surgical needle 10. (It should be understood that item 36 represents a distal portion of a needle holder, and one of skill in the art can select from among the many commonly available needle holders.) Surgical needle 10 is provided with a length of suture material 38 affixed within suture bore 18. Pointed tip 14 is positioned adjacent wall B and driven therethrough by rotating surgical needle 10 about its center of radius. As surgical needle 10 penetrates wall B it creates an entrance hole D in wall B. Surgical needle 10 is rotated such that it passes through lumen C and into lumen G in second vascular tissue section E.

Figure 3:
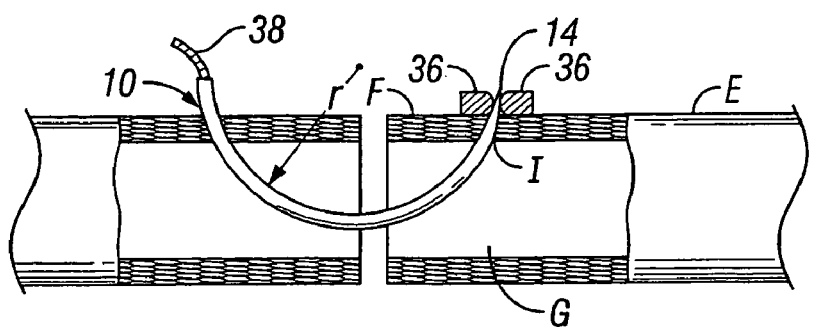

Now referring to FIG. 3, once a portion of surgical needle 10 has entered lumen G of second vascular tissue section E, surgical needle 10 is rotated further to penetrate wall F thereby causing an exit hole I to be created in wall F. Pointed tip 14 is then grasped with another needle holder 36 and the tail portion 16 is released from original needle holder 36. Thus, having penetrated through both first and second vascular tissue sections A and E, surgical needle 10 is ready to be withdrawn from vascular tissue sections A and E thereby drawing a length of suture material 38 through vascular tissue sections A and E to form a stitch.

Figure 4:
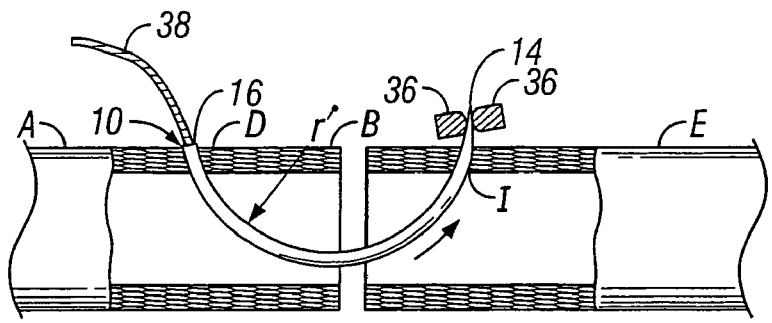

As shown in FIG. 4, to draw surgical needle 10 through vascular tissue sections A and E, surgical needle 10 is rotated further about its center of radius to draw a length of suture material 38 into lumen C.

Figure 5:
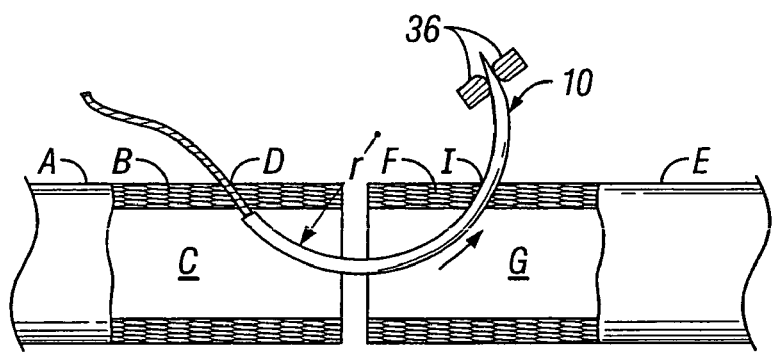
Figure 6:
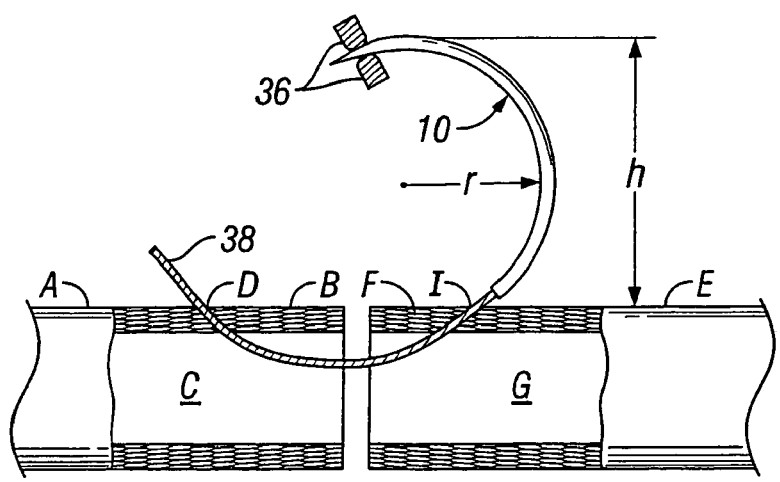

Referring to FIGS. 5 and 6, surgical needle 10 is rotated further to draw surgical needle 10 through lumens C and G, and out through exit hole I. This process draws length of suture material 38 through entrance and exit holes D and I to suture or stitch vascular tissue sections A and E together. With particular reference to FIG. 6, as surgical needle 10 is rotated out of vascular tissue section E, surgical needle 10 requires a significant amount of space in order to be manipulated, the height of this space is indicated by height "h." As can be appreciated, initial penetration of first vascular tissue section A also requires a significant amount of space. Thus, the suturing of vascular tissues with the prior art surgical suturing needle of the type shown as suturing needle 10 typically requires a significant amount of operating space adjacent the vascular tissue sections A and E in order to manipulate surgical needle 10.

Figure 7:
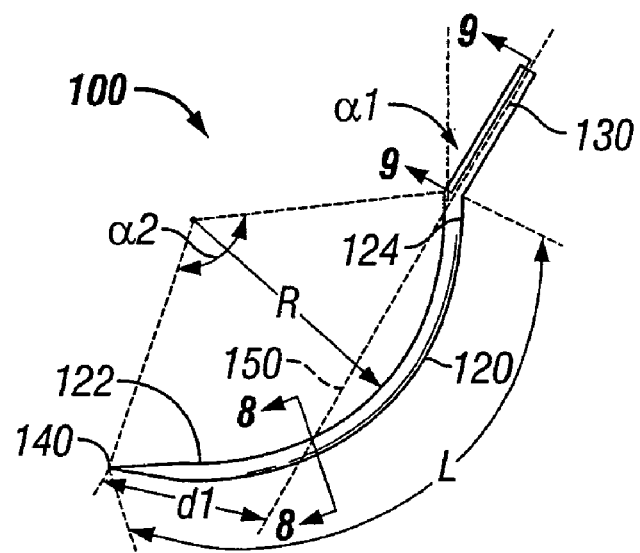
FIG. 7 is a front view of the surgical needle of the present disclosure.

FIG. 7 illustrates an embodiment of the surgical needle 100 of the present disclosure. Surgical needle 100 includes a generally arcuate portion 120 having a first end 122, a second end 124 and a radius "R." A pointed tip 140 is formed near first end 122 of arcuate portion 120 and a relatively straight shank 130 extends near second end 124 of arcuate portion 120. Arcuate portion 120 may be solid, hollow, partially hollow, channel-shaped, etc. Radius R is substantially larger than that used with known surgical suturing needles, such as prior art needle 10 described above, and gives a generally more flat profile to arcuate portion 120. Shank 130 forms a relatively abrupt juncture angle "α1" with a tangent of second end 124 of arcuate portion 120. As used herein the term "abrupt" indicates distinct transition as opposed to gradual melding of one portion into another. Juncture angle α1 is in the range of about 23° to about 29°, and in a particularly useful embodiment, is approximately 26°. As mentioned above, U.S. Pat. No. 5,891,164 discloses a surgical needle where the juncture angle is between 30° and 70°. An advantage of the present disclosure over this reference is that reducing the juncture angle allows the intersection (i.e., juncture) of the arcuate portion 120 and the shank 130, as well as the shank 130 itself, to more easily pass through the vascular tissue.

That is, as the juncture angle decreases, an extrapolation of a longitudinal axis 150 of shank 28 intersects arcuate portion 120 of surgical needle 100. This intersection may occur up to about 0.100 inches from the extrapolation line of the longitudinal axis 150 to pointed tip 140 of surgical needle 100, illustrated as "d1" in FIG. 7. The '164 reference discloses a surgical needle where the extrapolation line of shank does not intersect arcuate portion. The intersection of the present disclosure is advantageous because it may reduce the overall profile size of the surgical needle 100, particularly the juncture between the arcuate portion 120 and the shank 130, thereby allowing the juncture and shank 130 to more easily pass through the tissue and potentially reducing trauma to the tissue as the surgical needle 100 passes therethrough.

Radius R of the present disclosure may range from about 0.151 to about 0.171 inches and may be constant or variable over its entire length. Arcuate portion 120 of surgical needle 100 generally has an overall length L which may range from about 0.224 to about 0.343 inches, corresponding to arch angle α2 in the range of about 85° to about 115°. Shank 130 has a length which may range from about 0.078 inches to about 0.108 inches. Radius R, and thus arch angle α2, may be constant or varied along the length of arcuate portion. In the embodiment where arch angle α2 is constant, the angle may be in the range of about 85° to about 115°. In a particularly useful embodiment, the arch angle α2 may be approximately 100°. In the embodiment where the arch angle α2 varies, it may increase from below 100° (e.g., about 85°) at the second end of the arcuate portion to above 100° (e.g., about 115°) at the first end of the arcuate portion.

Figure 8:
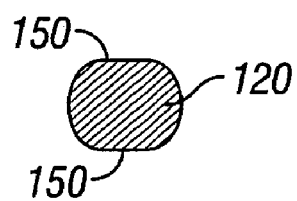
FIG. 8 is a cross-sectional view taken along line 8-8 of FIG. 7.

Referring to FIG. 8, cross-section of arcuate portion 120 of surgical needle 100 may be consistent or tapered. Arcuate portion 120 may have a generally circular cross-section adjacent pointed tip 140 and may also have relatively flat sides 150 to increase strength and facilitate use. At least one portion of cross-section of arcuate portion 120 may have a diameter of about 0.010 inches. In the embodiment where arcuate portion 120 has a cross-section of relatively flat sides 150, the diameter from one side 150 to opposing side 150 may be about 0.009 inches.

Figure 9:
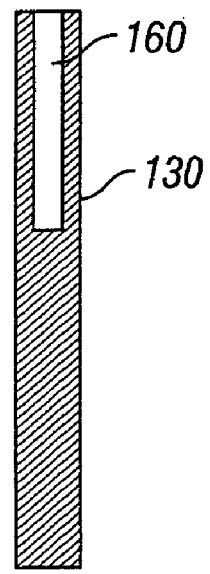
FIG. 9 is a cross-sectional view taken along line 9-9 of FIG. 7.

Now referring to FIG. 9, shank 130 has a generally circular cross-section and includes a bore 160 for suture attachment. Bore 160 is formed within shank 130 for receipt of an end of a length of suture material 170 (see FIGS. 10-14) therein. An end of the length of suture material 170 may be secured within bore 160 by known attaching techniques, such as, for example, crimping or use of surgical grade adhesives such as, for example, cyanoacrylate glue, epoxy cements or other medically acceptable adhesives. Length of bore 160 may be in the range of about 0.040 to about 0.050 inches.

Figure 10:
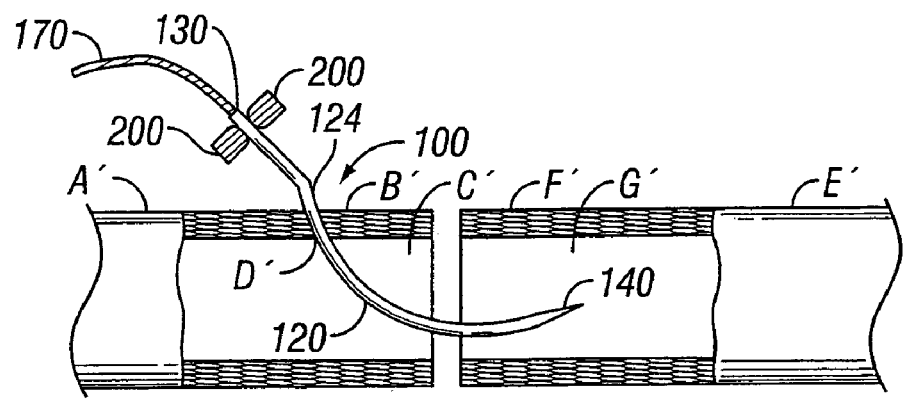
FIGS. 10-14 illustrate the surgical needle of FIG. 7 in various stages of being drawn through tissue.

Referring now to FIGS. 10-14, surgical needle 100 permits vascular tissue to be sutured using significantly less operating space than surgical needles of the prior art (FIGS. 1-6). Referring initially to FIG. 10, surgical needle 100, attached to suture material 170, may be utilized to suture together two opposed vascular tissue sections, such as, first vascular tissue section A' and second vascular tissue section E'. First vascular tissue section A' has an outer wall B' and defines a lumen C' therein. Second vascular tissue section E' has an outer wall F' and defines a lumen G' therein.

Initially, surgical needle 100 is grasped adjacent shank 130 by first needle holder 200. Pointed tip 140 is positioned adjacent wall B', moves through wall B' and into inner lumen C'. The radius R of arcuate portion 120 and straight shank 130 allow pointed tip 140 to be inserted into wall B' without it being necessary to rotate surgical needle 20 such a large distance, as practiced in the prior art (see FIGS. 1-6). As surgical needle 100 is passed through wall B' it creates an entrance hole D'. Surgical needle 100 can then be manipulated to advance arcuate portion 120 through entrance hole D' and to advance pointed tip 140 into lumen G' of second vascular tissue section E'. Surgical needle 100 is then manipulated to cause pointed tip 140 to penetrate wall F', creating an exit hole I'. The juncture angle α1 facilitates driving pointed tip 140 through wall F' with a minimal amount of rotational motion. At this stage of insertion, shank 130 is positioned flush with or substantially parallel to an outer surface of first vascular tissue section A' (see FIG. 11).

Figure 11:
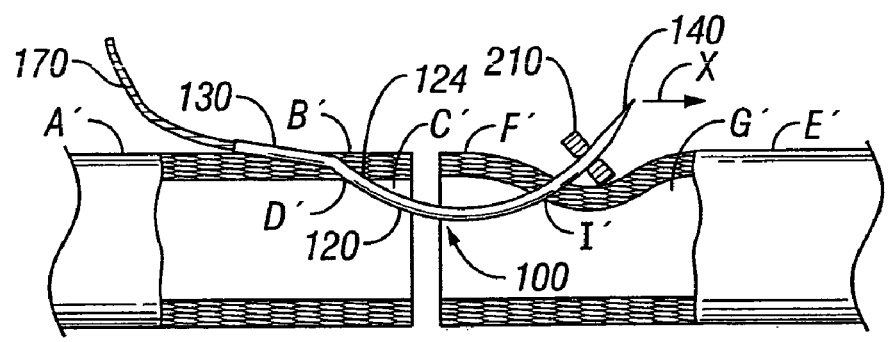

As best seen in FIG. 11, once pointed tip 140 has penetrated wall F' thereby creating exit hole I', shank 130 is released from the grasp of first needle holder 200 and pointed tip 140 is grasped by second needle holder 210. In contrast to the rotational motion used to move prior art surgical needle 10 through the vascular tissue sections, surgical needle 100 of the present disclosure is dimensioned and configured to be moved substantially parallel to the vascular tissue sections A' and E'. As shown in FIGS. 10-14, this motion of moving surgical needle 100 parallel to the vascular tissue sections A' and E' (as indicated by arrow X in FIGS. 11-13) requires a significantly smaller amount of operating space adjacent the vascular tissue sections A' and E'.

Figure 12:
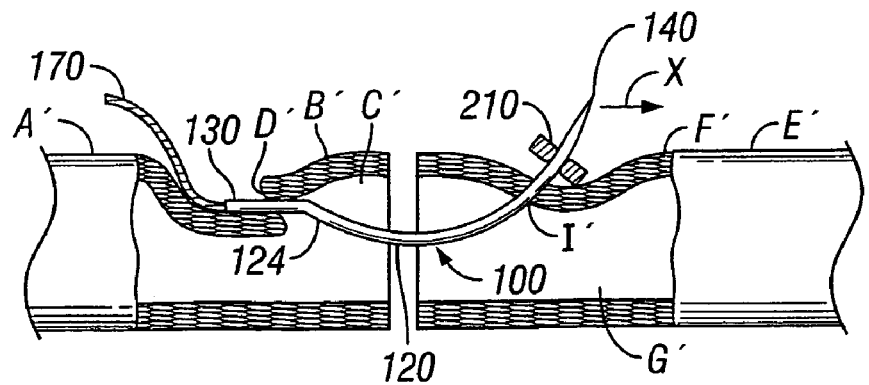

Referring now to FIG. 12, as pointed tip 140 is grasped by second needle holder 210 and moved substantially parallel to second vascular tissue section E' in general direction of arrow X, shank 130 is drawn through entrance hole D' in first vascular tissue section A'. This is facilitated by the juncture angle α1 which enables shank 130 to easily slide through entrance hole D' as pointed tip 140 is pulled substantially parallel to second vascular tissue section E'.

Figure 13:
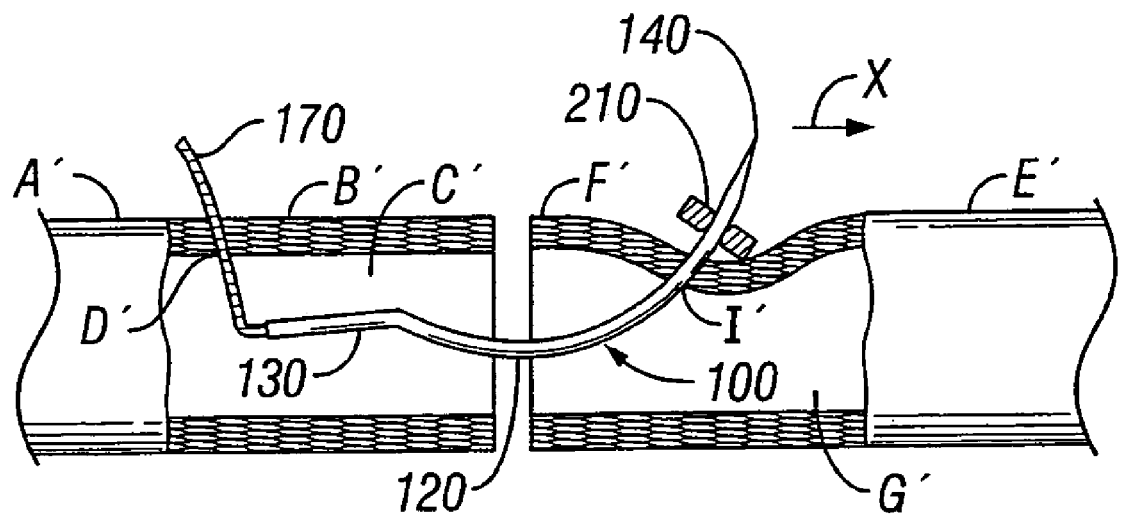

As shown in FIG. 13, once shank 130 has been drawn through entrance hole D', length of suture material 170 passes through entrance hole D'. Continued pulling of pointed tip 140 by second needle holder 210 substantially parallel to second vascular tissue section E' draws length of suture material 170 into and through lumens C' and G'.

Figure 14:
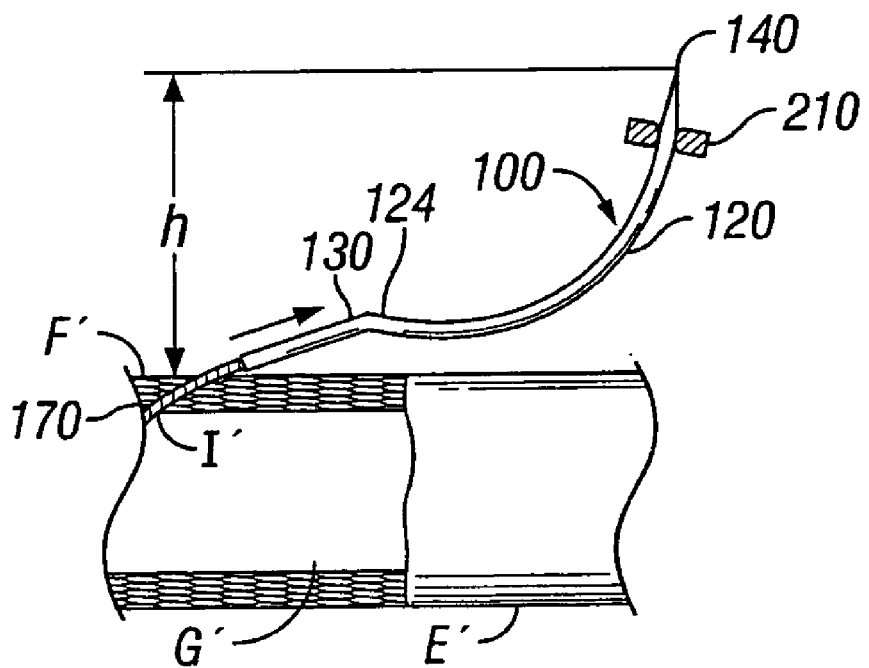

Continued pulling of pointed tip 140 draws surgical needle 100 out of lumen G', as shown in FIG. 14. The height H of the space necessary for surgical needle 100 to be manipulated is significantly less than that of height h illustrated in FIG. 6 with respect to prior art surgical needle 10, as discussed above.

While the above description contains many specifics, these specifics should not be construed as limitations on the scope of the present disclosure, but merely as exemplifications of various embodiments thereof. For example, it is envisioned that only one needle holder can be used to suture tissue, instead of the first and second needle holders disclosed. Those skilled in the art will envision many other possible variations that are within the scope and spirit of the present disclosure.

What is claimed:
1. A surgical suturing needle comprising:
an arcuate portion having a first end, a second end and a radius;
a pointed tip disposed near the first end of the arcuate portion; and
a relatively straight shank disposed adjacent the second end of the arcuate portion, the shank and the arcuate portion forming a juncture angle therebetween, the juncture angle being defined by a longitudinal axis of the shank and a tangent of the second end of the arcuate portion;
wherein an extrapolation of the longitudinal axis of the shank intersects the arcuate portion of the surgical needle up to about 0.100 inches from the pointed tip.
2. The surgical suturing needle according to claim 1, wherein the juncture angle is between about 23° and about 29°.

3. The surgical suturing needle according to claim 1, wherein a length of the shank is less than the radius of the arcuate portion.

4. The surgical suturing needle according to claim 1, wherein a length of the shank being in the range of about 0.078 inches to about 0.108 inches.

5. The surgical suturing needle according to claim 1, wherein at least a portion of the arcuate portion having at least one relatively flat side.

6. The surgical suturing needle according to claim 1, wherein the shank having a substantially circular cross-section.

7. The surgical suturing needle according to claim 1, wherein the shank further includes a bore which receives a portion of a suture material.

8. The surgical suturing needle according to claim 1, wherein an extrapolation of the longitudinal axis of the shank intersects the arcuate portion at about 0.100 inches from the pointed tip.

9. The surgical suturing needle according to claim 1, an arch angle of the arcuate portion is constant and is in the range of about 85° to about 115°.

10. The surgical suturing needle according to claim 1, wherein an arch angle of the arcuate portion is approximately 100°.

11. The surgical suturing needle according to claim 1, wherein the radius of the arcuate portion varies from its first end to its second end.

12. The surgical suturing needle according to claim 1, wherein the radius of the arcuate portion increases from its second end to its first end.

13. The surgical suturing needle according to claim 1, wherein an arch angle of the arcuate portion increases from about 85° at its second end to about 115° at its first end.

14. The surgical suturing needle according to claim 1, wherein an arch angle of the arcuate portion increase from below 100° at its second end to over 100° at its first end.

15. A method of suturing a first tissue section having a wall and defining a first lumen with a second tissue section having a wall and defining a second lumen, the method includes the steps of:
providing a surgical needle, the surgical needle comprising an arcuate portion having a first end, a second end and a radius, a pointed tip disposed adjacent the first end of the arcuate portion, and a relatively straight shank disposed adjacent the second end of the arcuate portion, the shank and the arcuate portion forming a juncture angle therebetween, the juncture angle being defined by a longitudinal axis of the shank and a tangent of the second end of the arcuate portion, wherein an extrapolation of the longitudinal axis of the shank intersects the arcuate portion of the surgical needle up to about 0.100 inches from the pointed tip;
providing a needle holder;
grasping the shank of the surgical needle with the needle holder;
forcing the pointed tip of the surgical needle against the wall of the first tissue section and driving the pointed tip into the first lumen;
advancing the pointed tip of the surgical needle through the first lumen and into the second lumen;
advancing the pointed tip of the surgical needle through the wall of the second lumen;
removing the needle holder from the shank of the surgical needle;
grasping the pointed tip of the surgical needle with the need holder; and pulling the surgical needle substantially parallel to the wall of the second lumen until at least a portion of the arcuate portion is removed from the second lumen.

* * * * *